(12) United States Patent
Wirth et al.

(10) Patent No.: US 12,340,897 B2
(45) Date of Patent: Jun. 24, 2025

(54) COPD MONITORING

(71) Applicant: KONINKLIJKE PHILIPS N.V., Eindhoven (NL)

(72) Inventors: Cristoph Tobias Wirth, Eindhoven (NL); Ioanna Sokoreli, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 200 days.

(21) Appl. No.: 17/988,261

(22) Filed: Nov. 16, 2022

(65) Prior Publication Data
US 2023/0207108 A1    Jun. 29, 2023

(30) Foreign Application Priority Data
Dec. 24, 2021   (EP) ..................................... 21217674

(51) Int. Cl.
*G16H 40/20*   (2018.01)
*G16H 50/50*   (2018.01)

(52) U.S. Cl.
CPC ............. *G16H 40/20* (2018.01); *G16H 50/50* (2018.01)

(58) Field of Classification Search
CPC ................................ G16H 40/20; G16H 50/50
See application file for complete search history.

(56) References Cited

U.S. PATENT DOCUMENTS

| | | | |
|---|---|---|---|
| 8,484,048 B2 * | 7/2013 | Halsted | G16H 40/63 705/3 |
| 2003/0009356 A1 * | 1/2003 | Hildebrand | G16H 40/67 705/2 |
| 2011/0071363 A1 * | 3/2011 | Montijo | G06Q 10/10 600/300 |

(Continued)

FOREIGN PATENT DOCUMENTS

| | | | |
|---|---|---|---|
| WO | WO-2006102549 A2 * | 9/2006 | G06Q 10/10 |
| WO | 2018158430 A1 | 9/2018 | |

(Continued)

OTHER PUBLICATIONS

Nicolini A, Mollar E, Grecchi B, Landucci N. Comparison of intermittent positive pressure breathing and temporary positive expiratory pressure in patients with severe chronic obstructive pulmonary disease. Arch Bronconeumol. Jan. 2014;50(1):18-24. doi: 10.1016/j.arbres.2013.07.019. Epub Dec. 8, 2013. (Year: 2014).*

(Continued)

*Primary Examiner* — Sun M Li
(74) *Attorney, Agent, or Firm* — Daniel H. Brean

(57) ABSTRACT

A system and method is provided for planning resources for a plurality of COPD RPM programs. Each RPM program is tailored to a different level of disease acuity. Assessment data is obtained relating to the severity of COPD symptoms in respect of a set of patients currently following one of the RPM programs. For each patient, a prediction is made of which RPM program is most likely to be appropriate for the patient at a future time point and from this a required (Continued)

capacity for each RPM program at said future time point can be derived. The required resources for each RPM program can thus be determined.

13 Claims, 7 Drawing Sheets

(56) References Cited

U.S. PATENT DOCUMENTS

| | | | |
|---|---|---|---|
| 2012/0047105 A1* | 2/2012 | Saigal | G16Z 99/00 706/54 |
| 2016/0004834 A1 | 1/2016 | Criner | |
| 2017/0024544 A1* | 1/2017 | Schmidt | G16H 20/70 |
| 2017/0325717 A1 | 11/2017 | Dellimore | |
| 2018/0314798 A1* | 11/2018 | Hernandez | G16H 50/30 |
| 2019/0180868 A1* | 6/2019 | Makram | G06N 20/00 |
| 2020/0135334 A1* | 4/2020 | Rajasekhar | G10L 15/26 |
| 2021/0174954 A1* | 6/2021 | Truschel | A61B 5/1118 |
| 2021/0407682 A1* | 12/2021 | Crossen | G16H 20/10 |

FOREIGN PATENT DOCUMENTS

| | | | | |
|---|---|---|---|---|
| WO | WO-2020081866 A1 * | 4/2020 | | G01N 33/6893 |
| WO | 2021127478 A1 | 6/2021 | | |

OTHER PUBLICATIONS

K. Gandy et al., "Remote Patient Monitoring: A Promising Digital Health Frontier," 2021 International Conference on Information and Digital Technologies (IDT), Zilina, Slovakia, 2021, pp. 297-302, doi: 10.1109/IDT52577.2021.9497599. (Year: 2021).*

U. R. V. S. Meenakshi and V. Jindal, "A Hybrid Feature Selection Model for Predicting Chronic Obstructive Pulmonary Disease," 2021 Third International Conference on Inventive Research in Computing Applications (ICIRCA), Coimbatore, India, 2021, pp. 589-596, doi: 10.1109/ICIRCA51532.2021.9544861. (Year: 2021).*

Nicolini, A. et al., "Comparison of Intermittent Positive Pressure Breathing and Temporary Positive Expiratory Pressure in Patients with Severe Chronic Obstructive Pulmonary Disease", Archivos de Bronconeumologia, vol. 50, No. 1 (2014), pp. 18-24.

Puente-Maestu, L. et al., "Health literacy and health outcomes in chronic obstructive pulmonary disease", Respiratory Medicine, vol. 115, (2016), pp. 78-82.

Ghobadi, H. et al., "The Relationship between COPD Assessment Test (CAT) Scores and Severity of Airflow Obstruction in Stable COPD Patients", Tanaffos (2012), pp. 22-26.

International Search Report for PCT/EP2022/086527 filed Dec. 18, 2022.

* cited by examiner

COPD MONITORING

CROSS-REFERENCE TO RELATED APPLICATIONS

This patent application claims the priority benefit under 35 U.S.C. § 119(a) of European Patent Application No. 21217674.7, filed on Dec. 24, 2021, the contents of which are hereby incorporated by reference.

FIELD OF THE INVENTION

The present invention relates to the field of monitoring chronic obstructive pulmonary disease (COPD), and in particular to the field of allocating patients to COPD remote patient monitoring (RPM) programs.

BACKGROUND OF THE INVENTION

Telehealth and remote patient monitoring solutions aim to reduce the frequency and severity of diseases exacerbations, to improve the quality of life of patients and to reduce resource use and cost for the health system. For example, telehealth and remote patient monitoring systems are used for managing patients with COPD.

There is a clear need for optimization of the remote monitoring offerings, for example for COPD patients.

RPM program managers generally either take into account the number of patients enrolled to a RPM program in order to estimate the resources needed to manage these patients, or else they enroll as many patients to a RPM program as possible to manage with the available resources. Resources for example include coaches who are supporting the patients throughout the RPM program via personal sessions, reviewing and managing flags and distributing devices to the patients needed for the RPM program. These devices are also part of the resources needed to run a RPM program efficiently.

RPM program managers estimate the resources needed to run a RPM program based on the currently available information, and they do not have any information relating to the future. For example, it is not known how many patients will be enrolled or graduate from a RPM program and their resource management cannot be optimized in advance. Hence, there is a limitation in the number of patients that can be enrolled in a RPM program at a given time and the resources available to support them.

One main challenge that RPM program managers are currently facing is that they cannot estimate the capacity management over a long timescale. They are managing the resources (coaches, devices etc.) and allocating them to the patients only based on past or current information available. This could possibly lead to a mismatch between the number of patients that would benefit by the RPM program and the number of resources available to support these patients.

Being able to predict how many patients will enroll, remain enrolled or graduate from a RPM program in the future would be of great help to RPM program managers to optimize resource allocation for example based on activity-based cost estimation, and optimally support as many patients as possible.

US 2020/135334 discloses a system for remote monitoring of chronic medical conditions such as COPD. Physiological parameters are monitored, compared with thresholds, and a level of severity is derived. An alert is generated for example so that a medical treatment is adjusted when needed.

SUMMARY OF THE INVENTION

The invention is defined by the claims.

According to examples in accordance with an aspect of the invention, there is provided a system for planning resources for a plurality of COPD RPM programs, each COPD RPM program being tailored to a different level of disease acuity, the system comprising:
  a processor adapted to:
  receive assessment data relating to the severity of COPD symptoms in respect of a set of patients currently following the RPM programs and/or in respect of a set of patients who are prospective eligible candidates for the RPM programs;
  for each patient, predicting which COPD RPM program is most likely to be appropriate for the patient at a future time point;
  determine a required capacity for each COPD RPM program at said future time point based on the predictions; and
  output data identifying the required resources for each COPD RPM program at said future time point.

This system predicts the number of patients that need to be enrolled to each RPM program in the future, by dynamically re-evaluating the disease severity status of the patients currently on each of the COPD RPM programs. This re-evaluation is based on a severity assessment, which is for example a set of modular assessment measures. Knowing how many patients will be enrolled to a particular RPM program and how many will graduate from the RPM program allows a RPM program manager to estimate a cost for resource management, or take preemptive action to re-allocate resources or hire new training RPM program coaches and manage devices.

In this way, the prospective required RPM program capacity can be predicted in advance so that RPM program managers can prepare their resource management in advance in order to optimally serve as many patients as possible with the right RPM program.

The system has a benefit for insurers in that there is a better indication of the cost of the RPM program in the future. Thus, an insurer has a more accurate estimation of the future cost of the RPM program based on activity (wherein an activity is a part of a RPM program) prediction.

The system has a benefit for the RPM program manager in that capacity management can be optimized because the RPM program manager can predict the required capacity of the RPM program and organize upfront the resources in order to optimize the care provided to the patients. The enrollment of new patients to the right RPM program can be optimized and it becomes known how many patients are graduating the RPM program.

The system also has benefits for the RPM program coaches in that the care management can be optimized. RPM program coaches usually need to manage many patients on the RPM program. Not all patients have the same needs. Knowing the number of the patients who are at risk of deteriorating in the future (moving to a higher acuity program) or who would probably graduate from this RPM program to a lower acuity one is very helpful to the coaches to estimate and prioritize the number of interactions they need to have with the patients in the RPM program. Knowing the number of patients who would need to be enrolled in the RPM program in the future helps them also estimate how many coaching sessions they would need to offer.

The system also has benefits for the patient, in that they receive the right care. Due to a limitation in resources (coaches and devices) there is a certain number of patients that could be enrolled in a RPM program at a time. Patients usually remain enrolled on this RPM program for a certain time period or till the end of the RPM program. However, if the patient's condition changes, the RPM program might no longer benefit the patient. On the other hand, other patients may benefit more from this RPM program while there is no place in the RPM program for them to enroll. The ability to better plan the future thus improves this situation.

The processor is for example further adapted to:
determine a required capacity for each COPD RPM program at a near term future time point based on the predictions; and
determine a required capacity for each COPD RPM program at a long term future time point based on the predictions.

The system thus provides advice in respect of two resource needs predictions (one short-term and one long-term) to allow the users (e.g. payer, RPM program manager) to estimate costs and organize resources for the two timelines.

The processor is for example adapted to derive a patient-level probability for each patient and for each RPM program at a future time point or time points, and combine the probabilities for all patients to derive a population distribution of patients per RPM program. Thus, the overall demand for a RPM program is derived from a combination of the probabilities of each patient requiring that RPM program at the future time point or time points.

The processor is for example adapted to derive a probability for each patient using a multinomial logistic regression.

The processor may be adapted to derive a cost budget for:
each RPM program; or
each of a set of resources ("activities") which together constitute the RPM programs.

Thus, not only is the future capacity demand modeled, but also the cost of managing the RPM programs at the required capacity.

The processor is for example adapted to determine a time-to availability for the required resources for each RPM program at said future time point. Thus, the ordering of resources can be planned to meet the predicted future resource requirements.

The assessment data for example comprises a severity measure for one or more of:
a COPD assessment test trend;
a COPD assessment test impact level;
a measure of a number of exacerbation events;
a disease severity measure; and
an oxygen saturation level,
wherein the processor is adapted to calculate a score which combines the plurality of severity measures of the assessment data and allocate the patient to a COPD RPM program based on at least the score.

The list of measures is non-exhaustive and other assessments may be used. Different assessments, or modules, can be switched on and off according to need.

The system thus aims to provide an improved allocation of patients to a RPM program. A RPM program is a long term program which monitors a patient's health over time and uses data which can change as a disease progresses. There may be a plurality of RPM programs, each designed for patients with a different severity of the disease. According to the invention, the patients are originally assessed with a base score level and associated to the right RPM program. Then, patients are periodically assessed so that they are placed in an optimal RPM program for their current state of health. Patients are therefore monitored and assistance can be given where necessary. By placing patients in the optimum RPM program, burdens on the service provider(s) are reduced by preventing that low acuity patients are monitored to a (higher)unnecessary level.

It has been realized that recurrent automated and optimized RPM program recommendation for COPD patients can facilitate better patient care. It is applicable to, and can use data from, any clinical setting such as primary care, hospital, insurance, GP systems, in-patient EMR and administrative claims from insurance. Furthermore it places little or no burden on the patient because it requires limited self-reported information and any self-reported information is simple and easy to obtain.

The present invention results in an increase in specificity and precision of follow up care provided to the patient because they are enrolled in the optimal RPM program for their needs. Some of the assessments may use data from a specific time, whereas some may use the change in data over time. This allows for trends, and changes in a patient's health to be taken into account and can help to anticipate how a patient's health may change.

The various severity measures each provide a different way of assessing the patient's health and relates to a different aspect such as the impact on quality of life, so that more aspects of a patient's quality of life are considered.

For each assessment a severity measure in the form of a raw score is provided. The raw score for each assessment may be based on the RPM program the patient is currently enrolled in. This helps to take into account the severity of the disease: if a patient is already in a medium acuity program and has exacerbations or interventions, it is more concerning than if a patient is currently in a low acuity program.

The disease severity based measure for example comprises the GOLD 1234 stage.

The plurality of RPM programs for example comprise a first type of RPM program for low acuity, a second type for medium acuity and a third type for high acuity. Thus, the patient may be dynamically reallocated between at least three different RPM programs depending on the patient's needs.

The processor is for example adapted to allocate a new patient to the first RPM program and to monitor the severity measures over an initial time period. This enables the patient's initial condition to be assessed.

The severity measure for the COPD assessment test trend is for example based on a measure of a gradient of a line of best fit to the COPD assessment test over time. Thus, it is a value indicating the trend of the CAT value.

The severity measure for the COPD assessment test impact level for example comprises a value for a low impact, a medium impact, a high impact and a very high impact. Thus, there are four possible values for the impact level.

The severity measure for the oxygen saturation level for example comprises value for a very low level, a low level and a normal level.

The invention also provides a computer-implemented method for planning resources for a plurality of COPD RPM programs, each COPD RPM program being tailored to a different level of disease acuity, the method comprising:
receiving assessment data relating to the severity of COPD symptoms in respect of a set of patients currently following the COPD RPM programs;
for each patient, predicting which COPD RPM program is most likely to be appropriate for the patient at a future time point;

determining a required capacity for each COPD RPM program at said future time point based on the predictions; and outputting data identifying the required resources for each COPD RPM program.

The invention also provides a computer program comprising computer program code means which is adapted, when said computer program is run on a computer, to implement the method defined above.

The invention also provides a processor which is programmed to implement the computer program.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
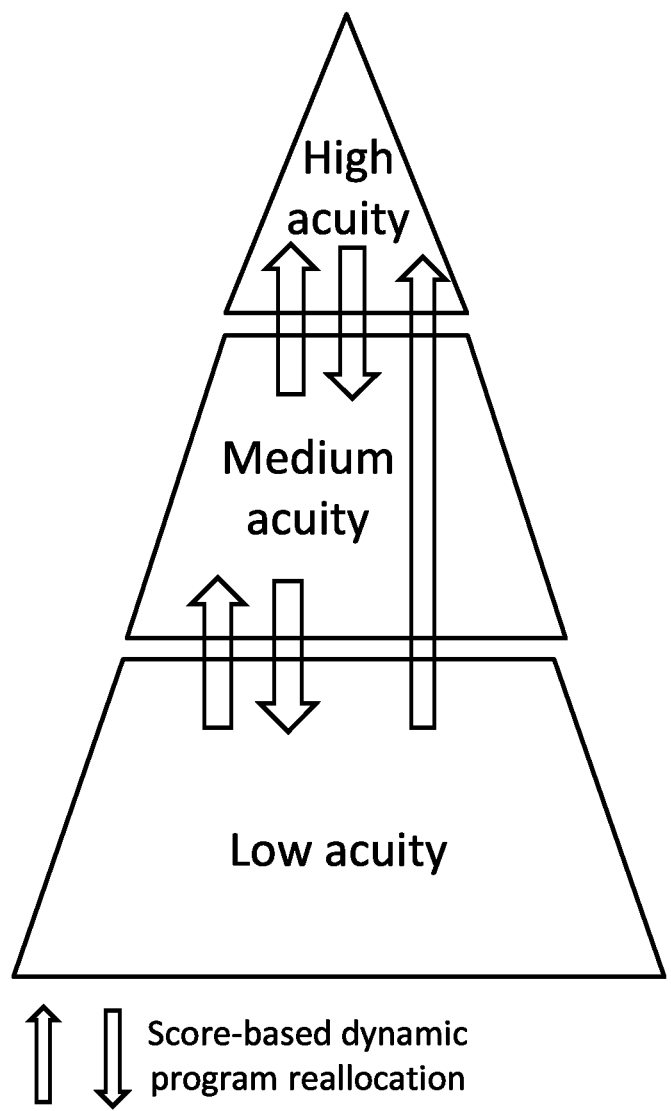
FIG. 1 is a diagram depicting RPM programs for different acuity levels.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings.

It should be understood that the Figures are merely schematic and are not drawn to scale. It should also be understood that the same reference numerals are used throughout the Figures to indicate the same or similar parts.

The invention provides a system and method for planning resources for a plurality of COPD RPM programs. Each COPD RPM program is tailored to a different level of disease acuity. Assessment data is obtained relating to the severity of COPD symptoms in respect of a set of patients currently following one of the COPD RPM programs. For each patient, a prediction is made of which COPD RPM program is most likely to be appropriate for the patient at a future time point and from this a required capacity for each COPD RPM program at said future time point can be derived. The required resources for each COPD RPM program can thus be determined.

FIG. 1 depicts different RPM programs related to different acuity levels of COPD disease.

In an example low acuity program, there may be personalized self-management with a COPD action plan and patient reported outcome measures (PROMs). There may be a patient education module to educate the patient about the symptoms of COPD and preventative measures. In a low acuity program, a patient may use their own device to manually enter data. On the basis of the PROMs, or other factors, the patient may initiate a request for primary care services.

A medium acuity program may include many, or all, of the support and monitoring features of a low acuity program but have additional support and monitoring. In an example of a medium acuity program there may again be a personalized self-management plan but instead of manual assessment data reporting and entry there may be automated data entry. In addition to patient-initiated ;requests for primary care services there may be scheduled healthcare appointments for example with a physician.

A high acuity program may include many, or all of the support and monitoring features but also have additional ones. There will be additional patient engagement and managed connected devices. There may be proactive intervention by telehealth services either in response to assessment data or at predetermined or random intervals.

Each patient is initially assessed for the disease acuity and placed into one of these three RPM programs based on the assessment of disease acuity. Previously, the patient remains on that RPM program for a certain time period or until the end of the RPM program regardless of the progress of the disease. It may be that a patient enrolled in a low acuity program deteriorates and would benefit from the additional monitoring and support available in a higher level RPM program. This can affect the health and quality of life of a patient because a higher level RPM program may identify problems earlier allowing preventative measures to be taken, thus avoiding more severe incidences and interventions.

Conversely a patient may be in a high level RPM program and their health has improved. The benefit of the RPM program is therefore very low because the level of monitoring and support offered is not necessary.

A first concept which has been devised by the inventors is to allow patients to be enrolled into the optimum acuity level of RPM program for any given point in time. This approach can also help to relieve problems related to RPM program capacity: a RPM program may be full, thereby preventing the enrolment of new patients, even though the benefit to some patients currently enrolled in this RPM program is low. By recurrent periodic re-evaluation of the acuity level of patients, they can be removed from unsuitable or inappropriate RPM programs (and enrolled in another RPM program) thus releasing capacity for patients for whom the RPM program would be more beneficial.

A recurrent re-assessment of a patient condition and re-allocation to the right RPM program can thus be performed. As can be seen from FIG. 1, a patient can move between acuity level RPM programs: more often between RPM programs of adjacent acuity but in more extreme cases directly from a low acuity program to a high acuity program. The transition between different RPM programs can occur at any time and is based on the acuity level and need of the patient.

FIG. 1 is illustrative and there may be more than three levels of RPM program and the present invention is applicable to any number of levels of RPM program.

Figure 2:
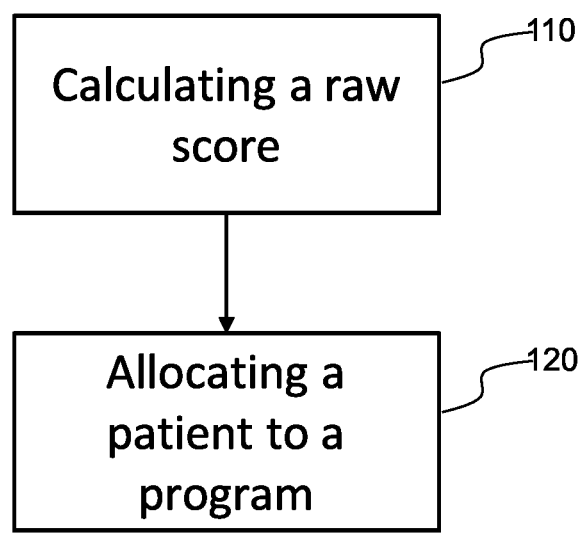
FIG. 2 depicts a method which may be used by a system which also incorporates the invention.

The dynamic allocation method which has been proposed by the inventors is depicted in FIG. 2 and comprises calculating in step 110 a score based on one or more assessments and in step 120 allocating a patient to a COPD RPM program based on at least the score. There may be a variety of assessments at different moments in time, and each assessment moment produces a score which can be used to allocate the patient to the appropriate RPM program level at that moment of time.

Each assessment involves making a severity measure for a respective indication of disease severity. As discussed below, a set of severity measures is used which may comprise or more of:
- a COPD assessment test (CAT) trend;
- a COPD assessment test impact level;
- a measure of a number of exacerbation events;
- a disease severity measure; and
- an oxygen saturation level.

In a preferred example, all five of these severity measures are used in combination.

On the basis of the resulting overall score, a patient is allocated, or reallocated to a specific COPD RPM program. The patient could be moved to a higher level RPM program or a lower level RPM program or remain in the same RPM program. Indeed a patient may be moved to a RPM program at a non-adjacent level.

Different types of assessment may be used: some may measure the absolute value, whereas some may assess a change, or trend over time.

The COPD Assessment Test (CAT) is a self-reported patient questionnaire used to measure the overall impact of COPD on a patient's health status. The assessment takes into account symptoms including cough, sputum, dyspnea and chest tightness. A CAT assessment comprises a series of statements and the patient indicates how much the statement describes them. As an example, relating to the symptom of coughing, a patient would indicate where on a scale of 0-5 they fit with I never cough being 0 and I cough all the time being 5. In one example CAT there are eight different questions. The CAT score is the total of all the questions. For a CAT with eight questions there is a maximum score of 40, which would indicate that COPD has a very severe impact on the patient's quality of life.

Figure 3A:
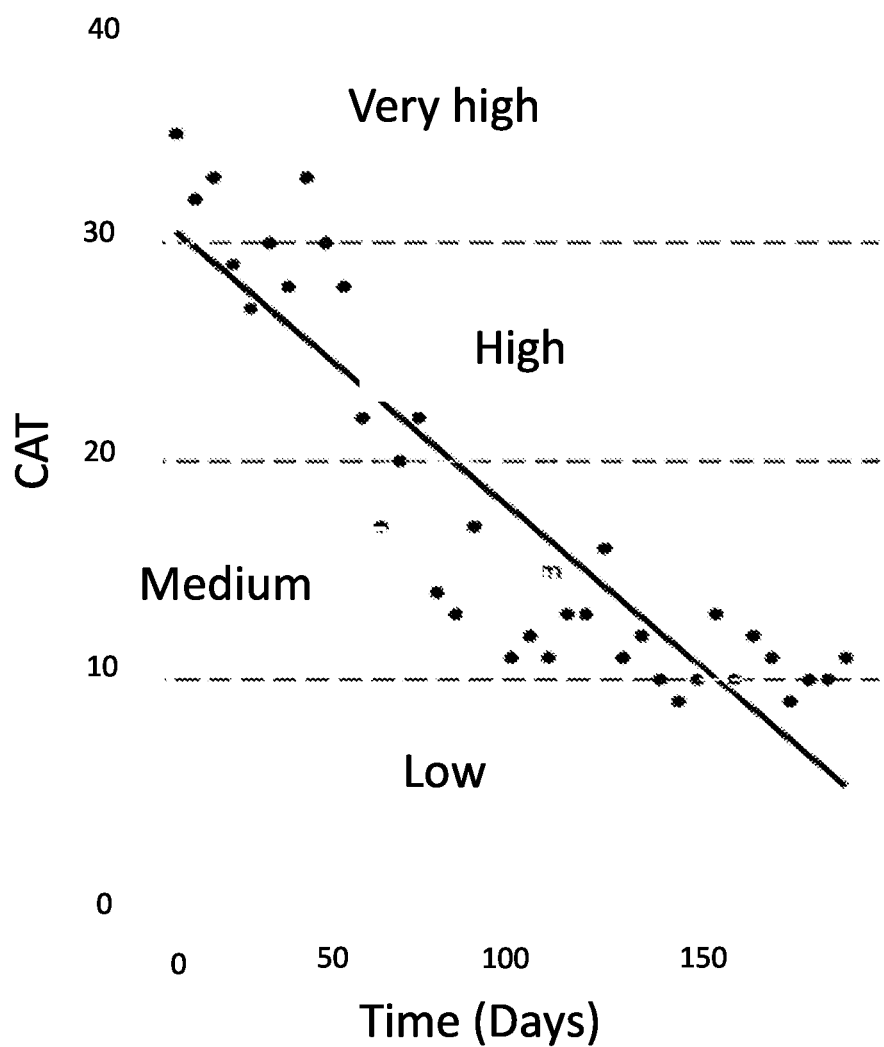
FIGS. 3A, 3B and 3C depict CAT trends.
Figure 3B:
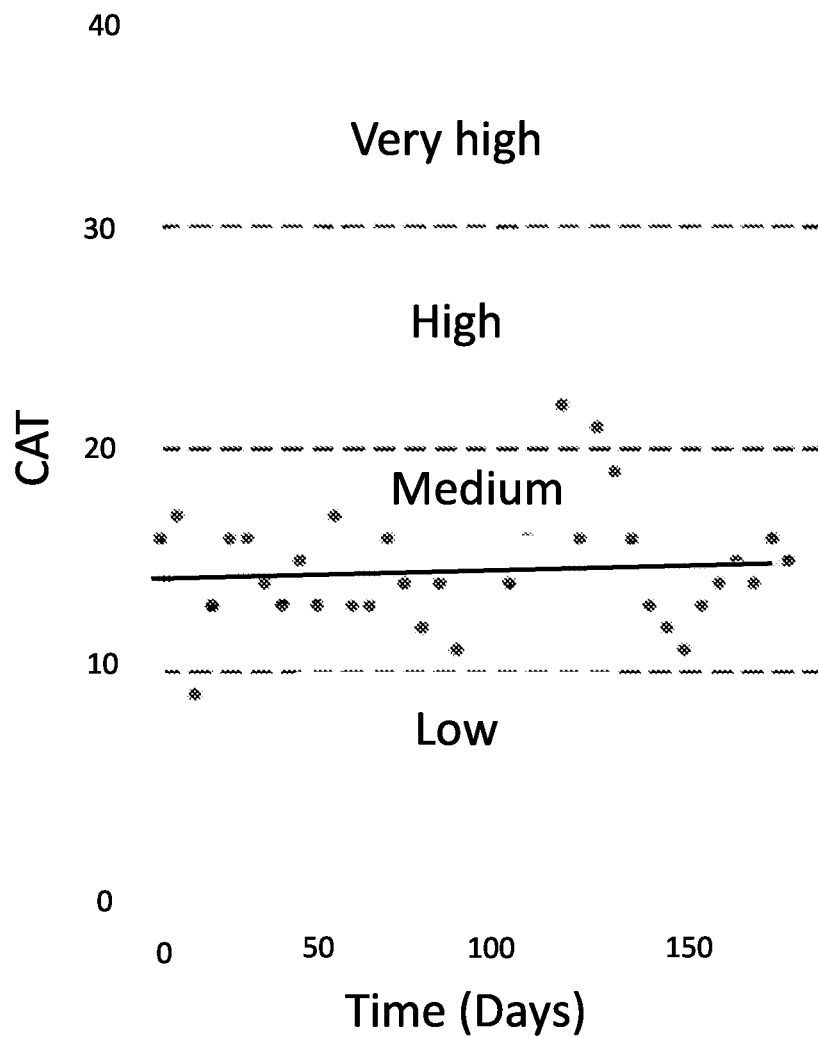
Figure 3C:
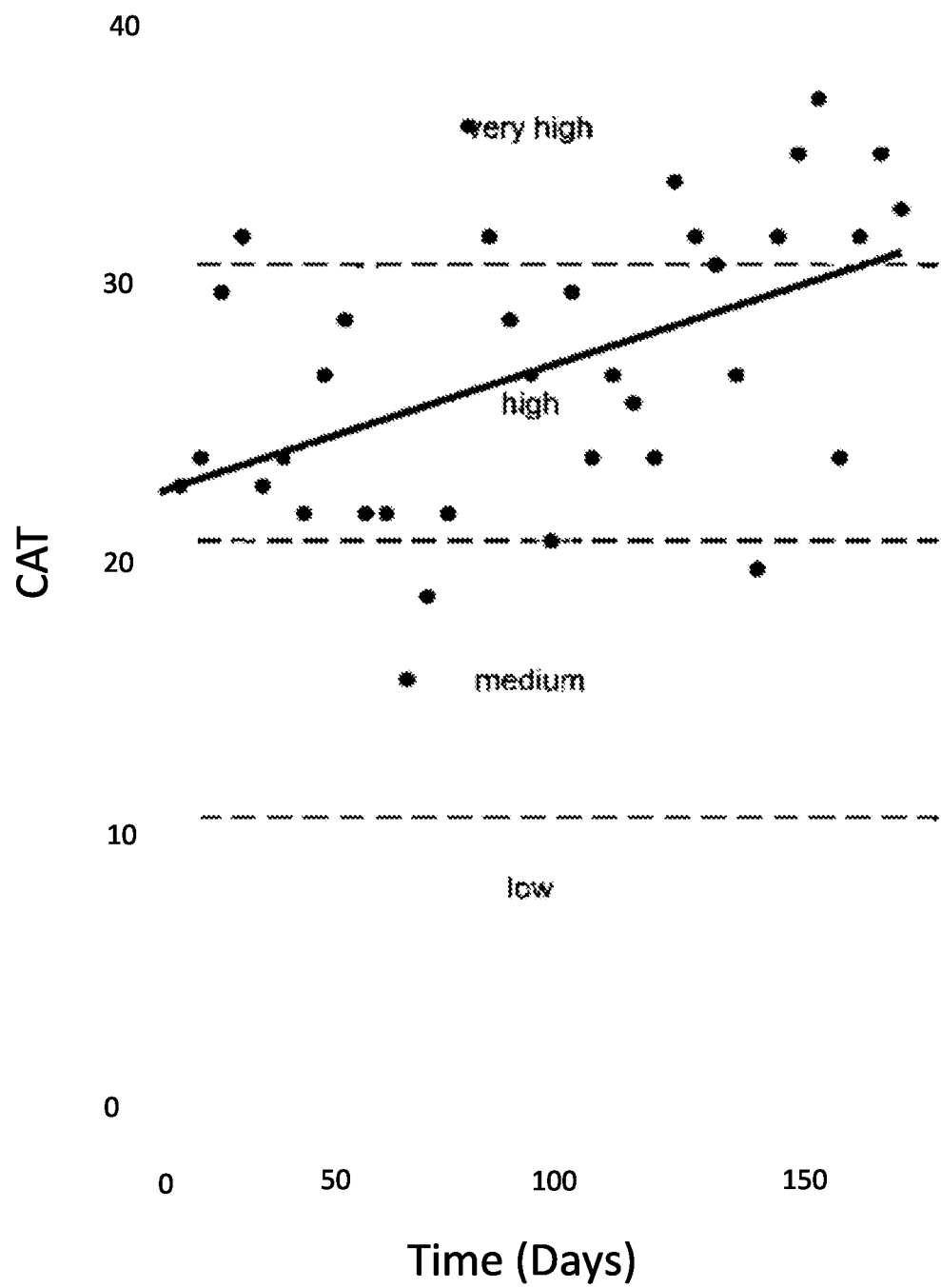

A CAT impact level assessment for the invention may group CAT scores into low impact, medium impact, high impact and very high impact. As an example:
- Low impact: CAT score<10 points
- Medium impact: 10 points≤CAT score≤20 points
- High impact: 20 points<CAT score≤30 points
- Very high impact: CAT score>30 points A CAT trend assessment assesses how the CAT result has changed over time. For example, the CAT result may improve, stay the same or worsen and this is depicted in FIGS. 3A, 3B and 3C respectively. The CAT trend assessment computes the slope of the CAT results of the evaluation period. The evaluation period may be since the beginning of the RPM program or another predetermined period—for example three months. A positive slope indicates a worsening of the patient's condition whereas a negative slope indicates an improvement in the patient's condition. A neutral slope (i.e. a zero slope within a tolerance range) indicates a stable condition during the evaluation period.

An assessment of exacerbations counts how many exacerbations there are in a predetermined period. An exacerbation is defined as an event leading to an admission to a hospital for COPD or two or more events which required a visit to a GP or medications but no hospitalization. The predetermined period over which the occurrence of exacerbations is examined can be a rolling three month basis. The exacerbations may be reported by the patient or taken from electronic medical records (EMR) or claims data.

A preferred example of a disease severity measure is the GOLD 1234 stage (Global initiative for chronic Obstructive Lung Disease). This is a method of classifying how severe COPD is for a patient and this can be used as an assessment for generating a raw score. There are four classifications (1234) which are based on the most recent spirometric assessment or alternatively the FEV1/FEV6 ratio measured by a handheld device. FEV1 indicates the amount of air forcefully exhaled in the first second of a six second test. FEV6 indicates the amount of air exhaled over the whole six seconds. The ratio FEV1/FEV6 gives an indication of the respiratory health of the patient with a higher result indicating better health.

More generally, disease severity can be derived from diagnostic spirometric assessment outcome metrics (e.g. GOLD 1234 stage, FEV1%, FEV1% predicted). It can be self-reported (e.g. questionnaire, mMRC grade), assessed via diagnostic classification coding system (e.g. ICD codes), or by physiological monitoring (e.g. handheld device measuring FEV1/FEV6), in particular by:
1. GOLD 1234 stage
2. FEV1% defined as FEV1/FVC ratio, also called Tiffeneau-Pinelli index
3. FEV1% predicted, which is defined as FEV1% of the patient divided by the average FEV1% for a person with similar characteristics
4. FEV1/FEV6 as a surrogate for FEV1/FVC measured by a handheld device
5. Diagnostic ICD codes for COPD (e.g. for ICD-10 classification of COPD codes J44.x.y with 3rd digit x (x=0, 1, 8, 9) and 4th digit y (y=0, 1, 2, 3, 9)
6. Severity grade of the Modified British Medical Research Council (mMRC) grade 0-IV As an example of a vital signs measurement, oxygen saturation can also be used as an assessment for a raw score. The most recent assessment of arterial blood oxygen saturation of the patient is used. This may be measured using a pulse oximetry device. The assessment may use the following three categories for measured oxygen levels:
- Very low: $SpO_2 \leq 90\%$
- Low: $91\% \leq SpO_2 \leq 94\%$
- Normal: $SpO_2 \geq 95\%$ Five different assessments are described above although the invention is not limited thereto and there may be other assessments additionally included.

The invention provides a prediction algorithm to estimate the optimal future program allocation of the patients and support the optimization of the resource allocation to improve the program execution. Thus, the invention makes use of the assessment information discussed above (which is used to allocate patients dynamically to a RPM program) additionally to predict a required future distribution of patients between different RPM programs, and hence predict a required future capacity of the different RPM programs.

When available resources for a RPM program are limited, the RPM program has a capacity limit corresponding to a certain patient volume. Each RPM program has required resources, such as devices, staff and IT equipment. If at a future moment, the new distribution of patients requires resources beyond the available resources, more resources are needed or else the certain patients will need to be delisted or remain in a lower acuity program.

Figure 4:
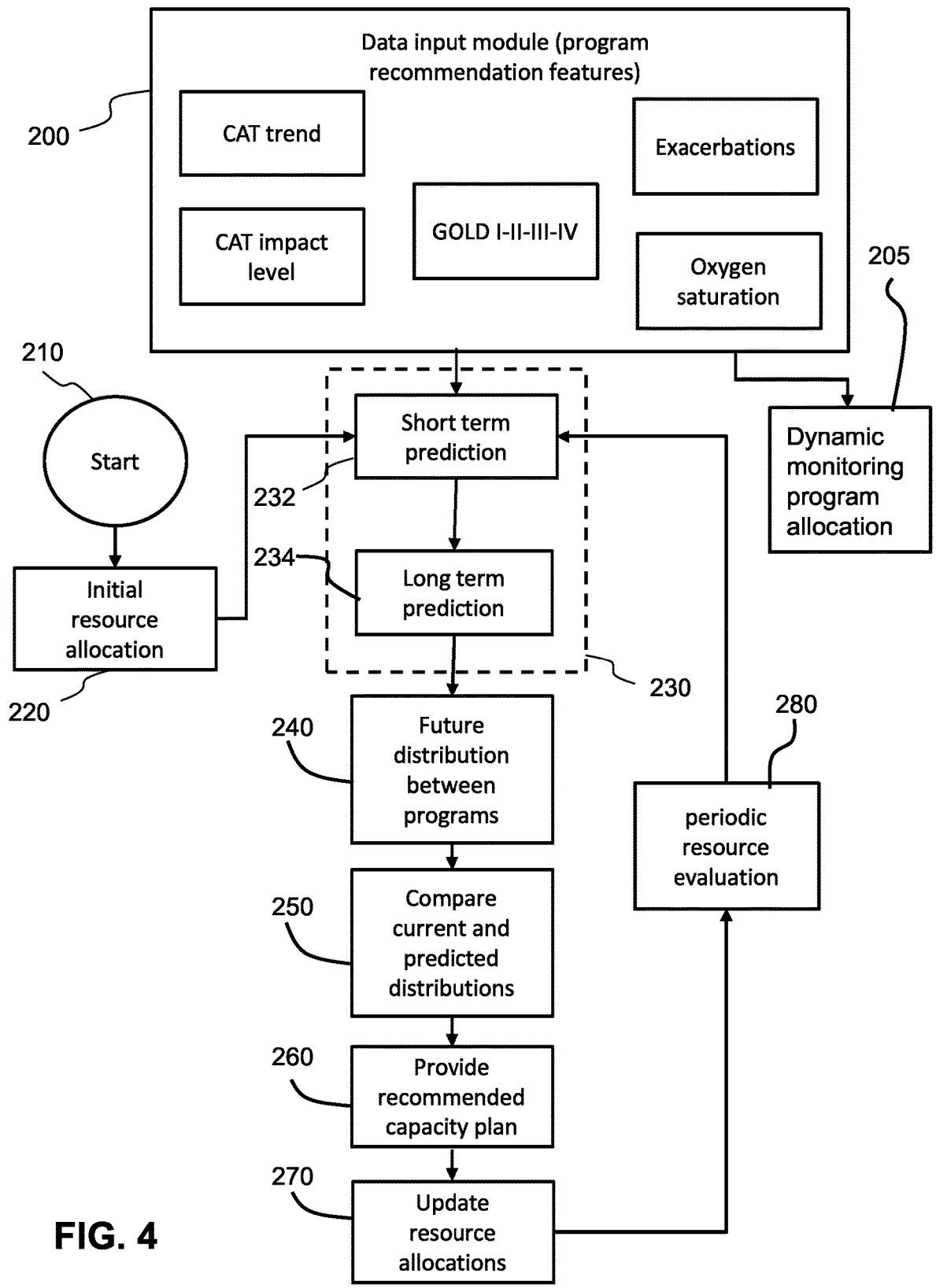
FIG. 4 depicts a method according to the invention.

The algorithm is schematically shown in FIG. 4. It may be used in conjunction with a system providing dynamic allocation of RPM programs as explained above.

There is a data input module 200 which comprises one or more assessment modules as discussed above. Data sources for the data input module can include clinical data from a GP, ambulatory or hospital EMR systems, administrative data sources such as claims data and from other modules collecting patient-reported data.

In this example and as explained above, the assessment modules comprise a CAT trend assessment module, a CAT impact level assessment module, a GOLD assessment module, an exacerbations module and an oxygen saturation module. These are used to provide input(s) to an algorithmic module 205 which takes raw scores from each of the assessment module and derives a total score which is used to determine which RPM program is suitable for the patients.

The use of the dynamic allocation as explained above results in an increase in specificity and precision of follow up care provided to the patient because they are enrolled in the correct RPM program. Some of the assessments may use data from a specific time, whereas some may use the change in data over time. This allows for trends, and changes in a patient's health to be taken into account and can help to anticipate how a patient's health may change.

The various severity measures each provide a different way of assessing the patient's health and relate to a different aspect such as the impact on quality of life, so that more aspects of a patient's quality of life are considered. The list of measures is non-exhaustive and other assessments may be used. Different assessments, or modules, can be switched on and off according to need.

For each assessment, a severity measure in the form of a raw score is provided. The raw score for each assessment may be based on the COPD RPM program the patient is currently enrolled in. This helps to take into account the severity of the disease: if a patient is already in a medium acuity program and has exacerbations or interventions, it is more concerning than if a patient is currently in a low acuity program. The current COPD RPM program may also be allocated a base severity measure. Each severity measure comprises a numeric value, and the numeric value depends on the current COPD RPM program. Thus, the severity measures take account of the current RPM program, thus they are able to encode whether the current RPM program is correct.

The score (i.e. the final score used to determine the appropriate RPM program), for example is based on the sum of the base severity measure and a cropped sum of the other severity measures. The cropping makes the final value fit to the range of possible RPM programs.

Advantages of the dynamic resource reallocation include recurrent automated and optimized resource allocation for the RPM programs. There is an improved efficiency of the number of patients enrolled and supported by the right RPM program at any moment in time. A modular approach allows users to activate or deactivate elements of interest to them. The execution is low cost and is applicable in any clinical setting such as primary care, hospital, insurance using GP ambulatory systems, in-patient EMR or administrative claims data from insurance. The system has little burden on the patient as it requires very limited self-reported information. It enables the need for care to be identified early.

The process starts in step 210. At the beginning of the method, all resources are allocated based on the currently known needs in step 220.

Following from this allocation, the method provides a periodic, recurrent, evaluation of the resource needs of the RPM programs based on a prediction of the number of patients that would be optimally enrolled to each RPM program in the future.

For this purpose, the data from the assessment modules in the data input module 200 is provided to a prediction unit 230. This comprises a short term prediction unit 232 and a long term prediction unit 234. It enables the future needed resources to be predicted to optimally run the RPM programs. Cost estimates may be provided, such as a cost estimate of the next quarter cost to the fee payer as well as estimates of longer term cost.

Both predictions of the future patients' acuity status are made based on the five assessment modules explained above: CAT trend, CAT score impact level, exacerbations, GOLD severity (I, II, III, IV) and oxygen saturation. A probability is derived based on this assessment and a recommendation is made for a RPM program change. The method thereby predicts if the patient may change to a lower of higher acuity program or stay in the same RPM program for a longer time.

A predicted future resource distribution between the different RPM programs can then be determined in step 240.

The RPM operations center is responsible for providing every patient a care RPM program addressing the patient's respective acuity level. The deployment and servicing of RPM programs requires resources (coaches, devices, IT, software, etc.). The type and intensity of resources depend on the RPM program's acuity level.

For simplifying the assessment it can be assumed that patients allocated to the same RPM program receives resources equal in type and intensity.

From the initial resource allocation in step 220, there is an initial distribution of patients across the different acuity levels of the RPM programs. This means there is an initial requirement on resources distributed across all RPM programs.

By re-evaluating the acuity level of the enrolled patients after every re-evaluation cycle, the right RPM program for each patient is re-determined. This means that after every re-evaluation cycle a new allocation of resources is required.

In step 250, the current distribution is compared with the future distribution. This enables a capacity plan to be derived in step 260.

For example, at the beginning of the method, if the resource volume of the initial allocation compared to the re-evaluation cycle is lower, new resources must be provided physically and added to the database.

Thus, resource allocations are updated in step 270 to meet the capacity plan. The resource allocations are output to the user of the system.

In other words, if demand on resources is higher than idle resources are available, an order for new resources must be placed. Depending on the nature of the resource (e.g. hiring a coach, device order) time is required. If the actual time to availability of new resource is unknown or too long, it will likely impact the delivery of effective care RPM programs.

For effective delivery of care programs, the RPM operations center must not only reduce the actual time to availability for resources but also it must know how many resources of a category need to be added at a determined moment in time.

In known systems, a database is used which contains logged information on the status of all available resources, which is resource in use (i.e. given to a patient allocated to a RPM program) and which resources are idle. The logging of resource status is accurate up to the present time.

By combining such a database with patient-level data acquired as explained above, a prescriptive method is provided, based on a patient allocation algorithm, in order to determine a future distribution of patients across programs. The prediction model now determines on a per-patient level how many resources will be required or become available for a future moment in time. The resources per RPM program can simply be determined by summing the resources used by all patients who are allocated to that RPM program.

The invention thus may be considered as an augmentation to an existing database using date relating to predicted required resources and available resources for a future moment in time based on the predicted allocation of patients to RPM programs. The difference between the predicted required resources and predicted available stocked resources per RPM program (in step 250) defines the new resources to be added.

Predicted available stocked resources contain already stocked resources and to-be-returned resources (e.g. from graduated or discharged patients). The database is thus extended using data on expected time to availability for all new resources by taking the assumed or estimated delivery time of a new resource.

The table below shows an example of resources (Device A, Device B and coaches) and the relevant information of the predicted future requirement, the predicted availability, the corresponding future requirement for additional resources (i.e. the difference) and the time to availability for those resources.

| Resource for program | Predicted required units at time t | Predicted available units at time t | New to be added units by time t | Expected time to availability |
|---|---|---|---|---|
| Device A | 250 | 10 | 240 | 5 weeks |
| Device B | 170 | 50 | 120 | 3 weeks |
| Coach | 2 | 1 | 1 | 4 weeks |

The resource allocation specialist or an automatic process is presented with the prediction output for ordering new resources in case the required demand is higher than available resources. As the algorithm is executable at any moment, the actual time for availability of new resources can be minimized or even zero at the time of program re-allocation which ensures timely allocation of patients to programs and resources and hence effective delivery of RPM programs.

In the example of the above table, the latest time for ordering 240 units of new Devices A would be 5 weeks ahead of the (predicted) RPM program re-allocation.

In another embodiment the predicted resources or program-related activities are taken into an activity-based cost model to predict the expected cost or needed budget for delivering the RPM program. If the predicted expected budget exceeds the available budget, a capacity plan is established to define capacity limits on patient volume per RPM program to ensure RPM program cost stay within budget.

The prediction is repeated periodically as represented by step 280, hence creating updated resource allocations in step 270 at each iteration. The re-evaluation of resource allocation may happen recurrently as frequently as the RPM program manager defines. Two resource needs predictions (one short-term and one long-term) are used to allow the users (payer, RPM program manager) to estimate costs and organize resources for the two timelines.

The algorithm can be implemented in a federated architecture which can be connected to patient records in GP (ambulatory, out-patient) software systems, hospital EMR systems or administrative claims data from a health insurer or care provider systems or to patient-reported data collection systems.

Some of the steps will now be described in more detail.

As explained above, the dynamic allocation involves calculating a patient-level probability (that the patient needs a particular RPM program) and it is used to recommend a RPM program change. All patient-level probabilities are combined to a population (aggregated) level distribution of estimated number of patients per RPM program.

The prediction module 230 can then calculate the dynamic patient-level RPM program allocation probability for future RPM programs. Thus, there is a prediction of which patients will upgrade their RPM program at the next evaluation step based on a set of input features:

Output: predicted RPM program level (categories: low, med, high) at next evaluation step (t):

$$Pred(t) = MODEL(input\ features)(t-1)$$

Input features:
CAT trend (t−1)
CAT impact level (t−1)
GOLD grade (t−1)
exacerbations (t−1)
$SpO_2$ (t−1)
enrolled RPM program at current time (t−1);
where t−1 is the time of assessment Thus, the assessment made by the severity measures provides an instantaneous indication of the most suitable RPM program. The model is used to extrapolate this information into the future.

For example, for a 3-level acuity program, the prediction model is a multinomial logistic regression where Pr is the predicted outcome probability, and K is the number of programs (in this case K=3) and β(k) is the vector of coefficients of the input features associated to outcome k.

The function of the model is a classification model that predicts a categorical response, for example multinomial logistic regression.

$$Pr(Y_i = 1) = \frac{e^{\beta'_1 * X_i}}{1 + \sum_{K=1}^{K-1} e^{\beta'_k * X_i}}$$

$$Pr(Y_i = 2) = \frac{e^{\beta'_2 * X_i}}{1 + \sum_{K=1}^{K-1} e^{\beta'_k * X_i}}$$

$$Pr(Y_i = K-1) = \frac{e^{\beta'_{K-1} * X_i}}{1 + \sum_{K=1}^{K-1} e^{\beta'_k * X_i}}$$

The model coefficients $\beta'_i$ can be trained for different time horizons oft (short-term, e.g. 3 weeks and long-term, e.g. for 3 months).

For each patient n, the program allocation probability for program p is given by:

$$Pr_n^p = \max_p Pr(Y_n = p)$$

This can be equivalently expressed as:

$$1_n^p(t) = \begin{cases} 1, & \text{patient } n \text{ is predicted for allocation to program } p \\ 0, & \text{patient } n \text{ is not predicted for allocation to program } p \end{cases}$$

where n denotes the patient, p the predicted program with p∈[1,K] and t the chosen time horizon of the prediction model.

$$Pr_n^p = \max_p Pr(Y_n = p)$$

The model works by based in a defined set of input features and a time horizon Any suitable trained multinomial response model may then be applied, for example computing probabilities for each potential program allocation and applying a rule to convert the e.g. 3 probabilities (0.3, 0.7, 0.1) into a program category (e.g. "medium").

Alternatively, any trained classifier model may be applied to the input features to obtain as output that RPM program to which the patient should be allocated (e.g. decision trees, Naive Bayes, Support Vector Machines, k-nearest neighbors, etc.).

For each RPM program, a service catalogue with patient-level costing is established, e.g. based on the computational framework in the table below where index p denotes program, i denotes the activity.

Similarly, the total expected resource allocation for an activity $\alpha_i$ can be computed as follows:

$$Resources_{expected}^{a_i} = \sum_n 1_n^p(t) \sum_p a_i^p$$

For example, the method can estimate upfront if additional full-time equivalent (FTE) telehealth nurses offering coaching sessions to patients are required for the next period when more patients are expected to be transitioned to higher intensity coaching RPM programs.

Likewise, the method estimates how many devices such as pulse oximeters or FEV1/FEV6 or handheld spirometers are to be ordered and issued to patients or will be returned for refurbishment.

When deploying the method in a new setting, a calibration phase is required. In this phase, feature data and output data (RPM program allocation of patients based on actual clinical decision) is collected for an initiation phase. This data is used to test and calibrate the predictive model in this setting in order to optimize the model performance.

| Service/ Activity ($a_i$) | Program (p) (High Medium Low) | Unit | Unit cost $uc_i^p$ | Event, quantity of units (N) | Frequency (f) of event recurrence in period (m) | Resource allocation $a_i^p$ | resource cost $cost_{a_i^p}$ |
|---|---|---|---|---|---|---|---|
| Coaching session | All | mins (min) | $/min | x | monthly≜ m | $a_i^p = N \cdot f$ | $cost_{a_i^p} = a_i^p \cdot uc_i^p$ |
| Returned devices for refurb | High/ medium | piece (pc) | $/pc | 1 | once≜ 1 | $a_i^p = N \cdot f$ | $cost_{a_i^p} = a_i^p \cdot uc_i^p$ |
| Newly issued devices | High/ medium | Piece (pc) | $/pc | 1 | once≜ 1 | $a_i^p = N \cdot f$ | $cost_{a_i^p} = a_i^p \cdot uc_i^p$ |
| Patient program introduction | all | session call (call) | $/call | 1 | once≜ 1 | $a_i^p = N \cdot f.$ | $cost_{a_i^p} = a_i^p \cdot uc_i^p$ |
| Enrollment process | all | process (proc) | $/proc | 1 | once≜ 1 | $a_i^p = N \cdot f$ | $cost_{a_i^p} = a_i^p \cdot uc_i^p$ |

Based on this table, a total expected budget can be computed for the next period attributable to a program p by summing up the costs of the total number of activities expected for the program to run:

$$Budget_{expected}^p = \sum_n 1_n^p(t) \sum_{a_i^p} cost_{a_i^p}$$

where $1_n^p$ takes a value 1 if patient n was predicted to be allocated to RPM program p at the next evaluation assessment and takes the value of 0 if the patient was allocated to a different RPM program. The total expected budget is the sum of all RPM program costs.

A calculation can also be made providing an estimation of the required budget for a selected activity (i.e. part of a RPM program).

This computation also allows to establish activity-based budget estimates for a selected activity. For example, it is possible to determine how much budget should be reserved for the ordering of newly to be issued devices as not all RPM programs will offer the full set of available devices. Higher acuity RPM programs will support more devices than just a self-management RPM program.

In one implementation of the invention, the assessment data may be obtained based on a minimal set of required interoperable data sources, for example relying on patient-reported data (hence single-source data) collected via a patient's interface device such as a smartphone. This makes the solution low cost and location-agnostic.

The system and method of the invention may thus be obtained using only patient-reported data.

Figure 5:
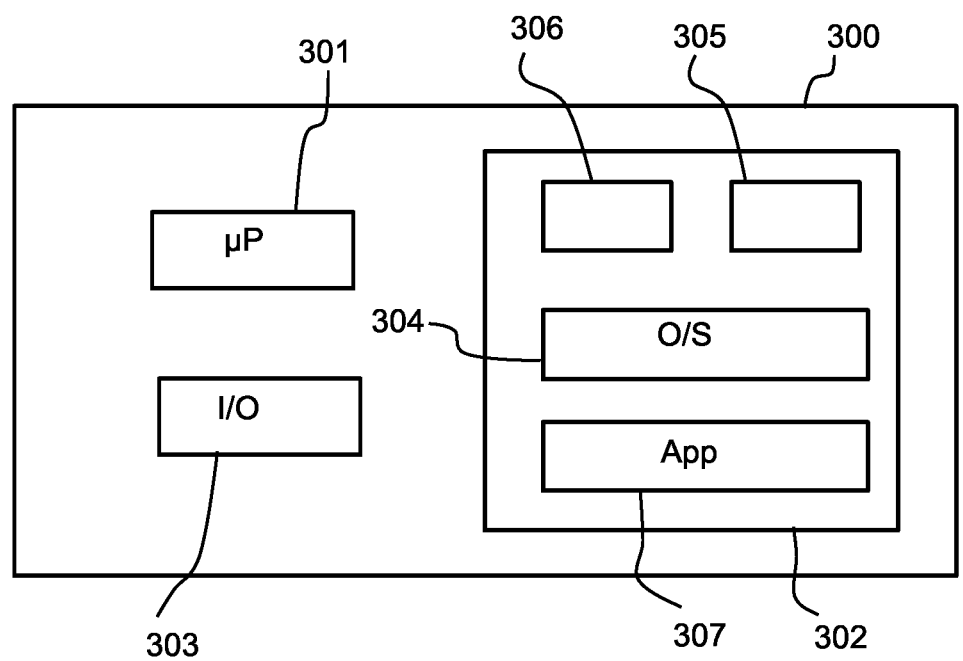
FIG. 5 is a simplified block diagram of a computer within which one or more parts of an embodiment may be employed.

FIG. 5 illustrates an example of a computer 300 within which one or more parts of an embodiment may be employed. Various operations discussed above may utilize the capabilities of the computer 300. For example, one or more parts of a system for providing a subject-specific user interface may be incorporated in any element, module, application, and/or component discussed herein. In this regard, it is to be understood that system functional blocks can run on a single computer or may be distributed over several computers and locations (e.g. connected via internet).

The computer 300 includes, but is not limited to, PCs, workstations, laptops, PDAs, palm devices, servers, storages, and the like. Generally, in terms of hardware architecture, the computer 300 may include one or more processors 301, memory 302, and one or more I/O devices 303 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 301 is a hardware device for executing software that can be stored in the memory 302. The processor 301 can be virtually any custom made or commercially available processor, a central processing unit (CPU), a digital signal processor (DSP), or an auxiliary processor among several processors associated with the computer 300, and the processor 301 may be a semiconductor based microprocessor (in the form of a microchip) or a microprocessor.

The memory 302 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 302 may incorporate electronic, magnetic, optical, and/or other types of storage media. Note that the memory 302 can have a distributed architecture, where various components are situated remote from one another, but can be accessed by the processor 301.

The software in the memory 302 may include one or more separate programs, each of which comprises an ordered listing of executable instructions for implementing logical functions. The software in the memory 302 includes a suitable operating system (O/S) 304, compiler 306, source code 305, and one or more applications 307 in accordance with exemplary embodiments. As illustrated, the application 307 comprises numerous functional components for implementing the features and operations of the exemplary embodiments. The application 307 of the computer 300 may represent various applications, computational units, logic, functional units, processes, operations, virtual entities, and/or modules in accordance with exemplary embodiments, but the application 307 is not meant to be a limitation.

The operating system 304 controls the execution of other computer programs, and provides scheduling, input-output control, file and data management, memory management, and communication control and related services. It is contemplated by the inventors that the application 307 for implementing exemplary embodiments may be applicable on all commercially available operating systems.

Application 307 may be a source program, executable program (object code), script, or any other entity comprising a set of instructions to be performed. When a source program, then the program is usually translated via a compiler (such as the compiler 306), assembler, interpreter, or the like, which may or may not be included within the memory 302, so as to operate properly in connection with the O/S 304. Furthermore, the application 307 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 303 may include input devices such as, for example but not limited to, a mouse, keyboard, scanner, microphone, camera, etc. Furthermore, the I/O devices 303 may also include output devices, for example but not limited to a printer, display, etc. Finally, the I/O devices 303 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 303 also include components for communicating over various networks, such as the Internet or intranet.

If the computer 300 is a PC, workstation, intelligent device or the like, the software in the memory 302 may further include a basic input output system (BIOS) (omitted for simplicity). The BIOS is a set of essential software routines that initialize and test hardware at startup, start the O/S 304, and support the transfer of data among the hardware devices. The BIOS is stored in some type of read-only-memory, such as ROM, PROM, EPROM, EEPROM or the like, so that the BIOS can be executed when the computer 300 is activated.

When the computer 300 is in operation, the processor 301 is configured to execute software stored within the memory 302, to communicate data to and from the memory 302, and to generally control operations of the computer 300 pursuant to the software. The application 307 and the O/S 304 are read, in whole or in part, by the processor 301, perhaps buffered within the processor 301, and then executed.

When the application 307 is implemented in software it should be noted that the application 307 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 307 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The proposed image capture and/or processing methods, may be implemented in hardware or software, or a mixture of both (for example, as firmware running on a hardware device). To the extent that an embodiment is implemented partly or wholly in software, the functional steps illustrated in the process flowcharts may be performed by suitably programmed physical computing devices, such as one or more central processing units (CPUs) or graphics processing units (GPUs). Each process—and its individual component steps as illustrated in the flowcharts—may be performed by the same or different computing devices. According to embodiments, a computer-readable storage medium stores a computer program comprising computer program code configured to cause one or more physical computing devices to carry out an encoding or decoding method as described above when the program is run on the one or more physical computing devices.

Storage media may include volatile and non-volatile computer memory such as RAM, PROM, EPROM, and EEPROM, optical discs (like CD, DVD, BD), magnetic storage media (like hard discs and tapes). Various storage media may be fixed within a computing device or may be transportable, such that the one or more programs stored thereon can be loaded into a processor.

To the extent that an embodiment is implemented partly or wholly in hardware, the blocks shown in the block diagrams of FIGS. 1 and 5 may be separate physical components, or logical subdivisions of single physical components, or may be all implemented in an integrated manner in one physical component. The functions of one block shown in the drawings may be divided between multiple components in an implementation, or the functions of multiple blocks shown in the drawings may be combined in single components in an implementation. Hardware components suitable for use in embodiments of the present invention include, but are not limited to, conventional microprocessors, application specific integrated circuits (ASICs), and field-programmable gate arrays (FPGAs). One or more blocks may be implemented as a combination of dedicated hardware to perform some functions and one or more programmed microprocessors and associated circuitry to perform other functions.

A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The invention claimed is:

1. A system for planning resources for a plurality of chronic obstructive pulmonary disease, COPD, remote patient monitoring, RPM, programs, each RPM program being tailored to a different level of disease acuity, the system comprising:
   a processor adapted to:
   receive assessment data relating to the severity of COPD symptoms in respect of a set of patients currently following the RPM programs and/or in respect of a set of patients who are prospective eligible candidates for the RPM programs, wherein the assessment data comprises a severity measure for one or more of:
   a COPD assessment test trend;
   a COPD assessment test impact level;
   a measure of a number of exacerbation events;
   a disease severity measure; and
   an oxygen saturation level;
   calculate a score which combines the plurality of severity measures of the assessment data and allocate the patient to a RPM program based on at least the score;
   for each patient, predict which RPM program is most likely to be appropriate for the patient at a future time point by applying a prediction algorithm to the assessment data to predict a required future distribution of patients between different RPM programs, wherein the predication algorithm comprises a function $$Pr(Y_i = K - 1) = \frac{e^{\beta_{K-1}^t * x_i}}{1 + \sum_{K=1}^{K-1} e^{\beta_k^t * x_i}},$$

where Pr is the predicted outcome probability, and K is the number of RPM programs, and β(k) is a vector of coefficients of input features associated to outcome k, wherein the input features are based on the assessment data, and a function $$Pr_n^p = \max_p Pr(Y_n = p),$$

wherein for each patient n, the program allocation probability for program p is given;
determine a required capacity for each RPM program at said future time point based on the program allocation probability; and
output data identifying the required resources for each RPM program at said future time point.

2. The system of claim 1, wherein the processor is further adapted to:
   determine a required capacity for each RPM program at a near term future time point based on the program allocation probability; and
   determine a required capacity for each RPM program at a long term future time point based on the program allocation probability.

3. The system of claim 1, wherein model coefficients $\beta_i^t$ are trained for different time horizons.

4. The system of claim 3, wherein the processor is adapted to derive a probability for each patient using a multinomial logistic regression.

5. The system of claim 1, wherein the processor is adapted to derive a cost budget for:
   each RPM program; or
   each of a set of resources which together constitute the RPM programs.

6. The system of claim 1, wherein the processor is adapted to determine a time-to availability for the required resources for each RPM program at said future time point.

7. The system of claim 1, wherein the plurality of RPM programs comprises a first RPM program for low acuity, a second RPM program for medium acuity and a third RPM program for high acuity.

8. The system of claim 1, wherein the severity measure for the COPD assessment test trend is based on a measure of a gradient of a line of best fit to a COPD assessment test value over time.

9. The system of claim 1, wherein the severity measure for the COPD assessment test impact level comprises a value for a low impact, a medium impact, a high impact and a very high impact.

10. The system of claim 1, wherein the severity measure for the oxygen saturation level comprises value for a very low level, a low level and a normal level.

11. The system of claim 1, wherein the processor is further adapted to receive an identification of a current RPM program to which a patient is currently allocated, wherein the current RPM program is allocated a base severity measure, and wherein each severity measure comprises a numeric value, wherein the numeric value depends on the current RPM program.

12. A computer-implemented method for planning resources for a plurality of chronic obstructive pulmonary disease, COPD, remote patient monitoring, RPM, programs, each RPM program being tailored to a different level of disease acuity, the method comprising:
   receiving assessment data relating to the severity of COPD symptoms in respect of a set of patients currently following one of the RPM programs, wherein the assessment data comprises a severity measure for one or more of:
      a COPD assessment test trend;
      a COPD assessment test impact level;
      a measure of a number of exacerbation events;
      a disease severity measure; and
      an oxygen saturation level;
   calculating a score which combines the plurality of severity measures of the assessment data and allocating the patient to a RPM program based on at least the score;
   for each patient, predicting which RPM program is most likely to be appropriate for the patient at a future time point by applying a prediction algorithm to the assessment data to predict a required future distribution of patients between different RPM programs, wherein the predication algorithm comprises a function $$Pr(Y_i = K - 1) = \frac{e^{\beta_{K-1}^t * X_i}}{1 + \sum_{K=1}^{K-1} e^{\beta_k^t * X_i}},$$

where Pr is the predicted outcome probability, and K is the number of RPM programs, and β(k) is a vector of coefficients of input features associated to outcome k, wherein the input features are based on the assessment data, and a function $$Pr_n^p = \max_p Pr(Y_n = p),$$

wherein for each patient n, the program allocation probability for program p is given;
   determining a required capacity for each RPM program at said future time point based on the program allocation probability; and
   outputting data identifying the required resources for each RPM program.

13. A computer program comprising computer program code means which is adapted, when said computer program is run on a computer, to implement the method of claim 12.

* * * * *